United States Patent [19]

McGinn

[11] Patent Number: 5,099,689
[45] Date of Patent: Mar. 31, 1992

[54] APPARATUS FOR DETERMINING THE EFFECTIVE FORCE APPLIED BY AN OARSMAN

[75] Inventor: John H. McGinn, Wynnewood, Pa.

[73] Assignee: Nielsen-Kellerman Company, Marcus Hook, Pa.

[21] Appl. No.: 615,063

[22] Filed: Nov. 19, 1990

[51] Int. Cl.⁵ .......................... A61B 5/22; A63B 69/06
[52] U.S. Cl. ........................................... 73/379; 482/72
[58] Field of Search ............... 73/379, 380, 862.09; 272/72, 144, DIG. 5, DIG. 6, 145, 146

[56] References Cited

FOREIGN PATENT DOCUMENTS

| 2335544 | 1/1975 | Fed. Rep. of Germany | 272/72 |
| 178577 | 7/1935 | Switzerland | 272/72 |
| 1223932 | 4/1986 | U.S.S.R. | 272/72 |

Primary Examiner—Charles A. Ruehl
Assistant Examiner—Elizabeth Shopbell
Attorney, Agent, or Firm—Woodcock, Washburn, Kurtz, Mackiewicz & Norris

[57] ABSTRACT

Methods and apparatus for determining the effective force generated by an athlete acting upon a rowing apparatus are disclosed. A flexural member attached to the rowing apparatus and a footboard hingably attached to the flexural member at its upper end and slidably attached to the rowing apparatus at its lower end are provided. The flexural member is fitted with strain gauges which produce a signal indicative of the strain in the flexural member, this signal can then be converted to a measure of the effective force applied to the oars. Most preferably, apparatus of the present invention substantially eliminates the effects of residual torque friction, thermal deformation and the like by isolating the flexural member from which strain data is taken.

20 Claims, 3 Drawing Sheets

APPARATUS FOR DETERMINING THE EFFECTIVE FORCE APPLIED BY AN OARSMAN

BACKGROUND OF THE INVENTION

The selection and training of oarsmen in the sport of competitive rowing would be greatly facilitated by on-water measurements providing quantitative data from which the individual as well as the collective performance of the crew members can be determined. A fundamental quantity for the assessment of performance is the effective force which an oarsman exerts on the oar handle or, alternatively, the reactive force produced by the oarsman's feet pushing on the stretcher of the rowing shell, exercise machine or other rowing apparatus. It would therefore be desirable to provide a device which produces a signal that is proportional to this effective force. By definition, the "effective force" is the longitudinal (axial) component of the applied force. It is this component which is responsible for the propulsion of the rowing shell. Therefore, it would further be desirable to provide apparatus that measures effective force while the shell is in use, i.e., "on-water" in addition to being useful in rowing simulators or other equipment.

The on-water measurements of rowing performance reported to date have primarily been the result of research programs relating to the biomechanical aspects of rowing. The apparatus involved in these studies has been generally quite complex and sophisticated. These investigations cover a wide range of variables and are geared to measuring a multitude of forces such as the forces acting on the oar, the oar locks, and, to a lesser extent, on the foot stretcher. These data are generally reported relative to a time base or as averages taken over specific time intervals. For example, force measurements obtained from the oar locks are frequently used to calculate the work done and/or the power developed by an oarsman. However, no practical device has been developed that can be used onwater for crew selection and for routine training purposes using either on-water tests or using rowing simulators.

A system designed by the inventor of the present invention and used by the University of Pennsylvania varsity crew team from 1964 to 1966 made use of an oarlock that was specially constructed to be restricted to move only in the longitudinal direction by a mechanical slide. Displacement of the oarlock and slide assembly compressed a spring and caused the sequential closing of four switches at predetermined force levels. Each oarsman was provided with a set of four lights; the first light was activated at a threshold force of 200 pounds of force and the other three lights were activated sequentially in increments of 25 pounds. A panel containing the composite readout for all eight oarsman could be viewed by the coxswain or from the coach's launch. The use of this system was discontinued due to the extensive maintenance required for the electromechanical components.

The apparatus discussed immediately above provided measurements of the force acting on the oarlock, and though it can be used for research purposes, it has many practical disadvantages. First, the oarlock must be modified in order to incorporate a linear sensing element. Further, some mechanical or electrical apparatus must be added to the oarlock in order to measure the longitudinal component of the applied force. The most serious drawback, however, is the difficulty in transferring the modified oarlock arrangement from one shell to another, as would be necessary, for example, if both heavyweight and lightweight crews were to be evaluated. Another major problem, as explained above, is the vulnerability of the modified lock and the associated wiring to mechanical damage. Finally, if the shell is rigged for sculling, both oarlocks should be instrumented, adding to the cost and complexity of the system.

Others have attempted to measure force using the oar itself as an elastic member to make force measurements. From a practical viewpoint, however, there are many serious objections to this scheme, quite aside from the difficulty of affixing a strain sensing element to the oar. First, the determination of the effective force exerted by the oarsman requires continuous measurement of the angular displacement of the oar. Therefore, some type of displacement resolution must be incorporated into this type of force measurement system. Secondly, both the sensing element and the wiring connecting it to the shell are extremely vulnerable, especially since the electrical connections to the oars must be disconnected when the boat is stored after a workout. Also, there is the problem of calibration since the elastic properties of the materials used in shells and oars are often sensitive to temperature. Finally, for sculling, both oars should be instrumented if the information relating to the performance is to be complete.

Thus, there remains an unmet need for apparatus capable of accurately measuring the force applied to an oar. In order to overcome the shortcomings of the prior art, such a system should be rugged and reliable, while altering the standard shell arrangement as little as possible.

SUMMARY OF THE INVENTION

It has now been found, however, that by providing specially adapted footboard apparatus from which precise deflection measurements can be taken, effective force measurements can be accurately determined. The present invention provides apparatus for determining the effective force generated by an athlete acting upon a rowing apparatus and comprises a flexural member attached to the rowing apparatus and a footboard hingably attached to the flexural member at its upper end and slidably attached to the rowing apparatus at its lower end. The physical arrangement of these components within the apparatus permits certain parameters such as deflection over a known length to be accurately measured and converted into a measure of the effective force. Preferably, strain gauges are affixed to the flexural member to produce a signal indicative of the strain therein, and this signal is then converted into a measure of the effective force. The apparatus of the present invention is applicable to a variety of rowing apparatus including the numerous types and styles of shells, as well as exercise machine or other rowing simulators.

In a preferred embodiment, the flexural member is a tubular member that has two ends, each of which is fitted with an end plug that attaches it to the rowing apparatus, and thereby defines a predetermined length over which the flexural member may deflect upon the application of a force upon the footboard. Most preferably, the apparatus is designed so that the torque created between the flexural member and the rowing apparatus by the force applied is substantially eliminated, thereby ensuring the accuracy of the effective force determination. The footboard is preferably attached to the rowing apparatus by the sliding engagement of a T-shaped member and a slot. Most preferably the T-shaped member is threaded and is retained within the slot by a nut threaded on to the T-shaped member and a bushing, while remaining free to slide in the longitudinal direction.

The signal generated by the strain gauges used in preferred embodiments of the present invention may be processed and displayed in any of a number of ways. For example, in certain embodiments, the apparatus of the present invention includes means for converting the strain gauge signal to a signal indicative of the effective force. This signal may then either transmitted to a display means or transmitted to means for storing data, or both.

In certain embodiments, the present invention also includes methods for determining the effective force generated by an athlete acting upon a rowing apparatus comprising the steps of providing a footboard hingably attached at its upper end to a flexural member that is attached to the rowing apparatus, and slidably attached to the rowing apparatus at its lower end. Next, the strain in the flexural member is determined and a signal is produced which is indicative of that strain. Finally, the signal is converted to a signal indicative of the effective force, which may be displayed or stored, or both.

DETAILED DESCRIPTION OF THE PREFERRED EMBODIMENTS

Figure 2:
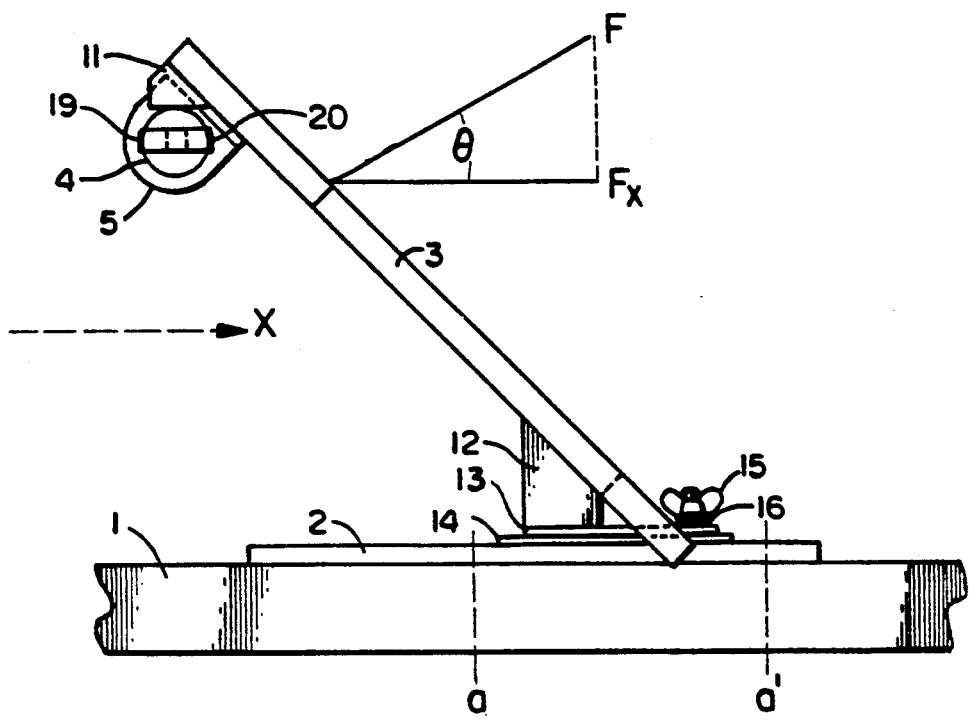
FIG. 2 is a side elevation view of a footboard, support member and other apparatus made in accordance with the present invention.

The most definitive single measurement for the determination of rowing performance is the effective force exerted by the oarsman on the foot stretcher. Referring first to FIG. 2, a foot stretcher assembly and its attachment to the keel 1 of a shell or other rowing apparatus are illustrated, as well as vectors illustrating the direction of the forces generated while rowing. As shown, the longitudinal direction, i.e., along the length of the shell, is designated the X direction. The force triangle illustrates that the overall force F applied against the foot stretcher may be resolved into a longitudinal component $F_x$; $F_x = F \cos \theta$, where $\theta$ is the angle between the force vector and the longitudinal axis (x-axis) of the shell. The effective, or longitudinal component, $F_x$, of the applied force, F, includes not only the reaction to the effective force acting on the oar grip, but also the forces arising from the acceleration of the oarsman's center of gravity, as well as that of the boat itself. If the net effective force F on the stretcher is known as a function of time, then the impulse imparted per stroke is equal to the area under this curve taken over a time, t, for one complete stroke cycle. Mathematically this value is found by integrating $F_x$ versus time, t, over a complete stroke cycle. A stroke cycle comprises the time of pulling of the oars through the water and the time during which they are returned to their starting position. If desired, the integration can be taken over any number of stroke cycles to obtain an average impulse. The magnitude of the impulse provides a quantitative measure of the performance of any one oarsman relative to others in the boat. Thus, the coach is provided with a criterion for crew selection. Further, the shape of the force-time curve furnishes qualitative information concerning the oarsman's style of rowing and hence also has a diagnostic value for training purposes. With experience, a coach or trainer can review force-time curves for various crew members and more accurately match the members into competitive teams.

Figure 1:
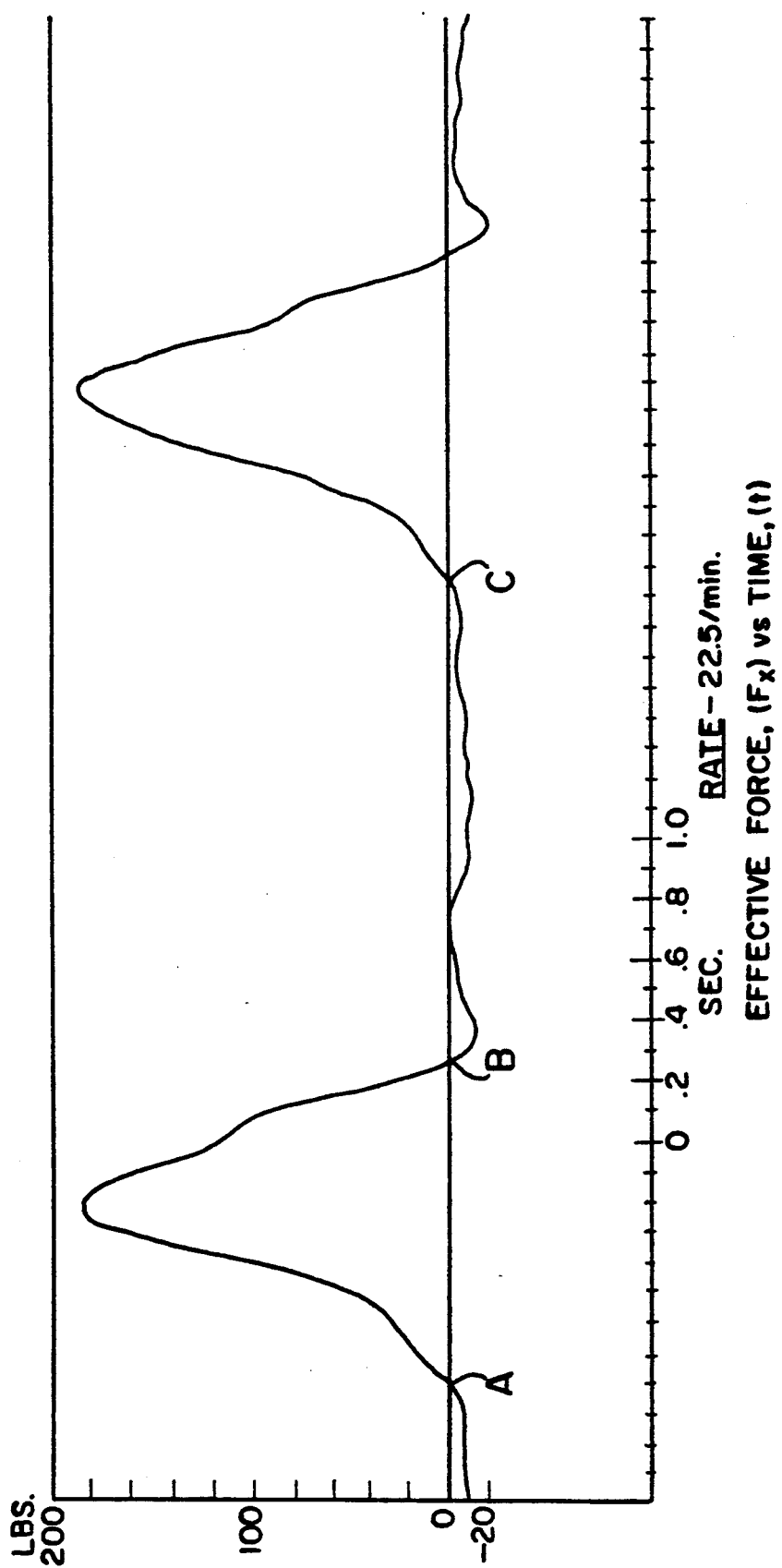
FIG. 1 is a graphic plot of the effective force applied by an oarsman over time, generated using the present invention.

A sample portion of an actual force-time curve for an oarsman generated using the present invention is shown in FIG. 1. The impulse generated when the oarsman is pulling the oar, i.e., during the "drive" portion of the stroke, is equal to the area under the portion of the curve from A to B. It should be noted that the area of the portion from B to C is the impulse generated during the "recovery" phase of the stroke. Those of ordinary skill will appreciate that force measurements made on the grip or oarlock do not account for this contribution, thus the stretcher force measurements are needed to calculate the total impulse imparted to the boat. In effect, an oarsman is doing work on the recovery as well as during the drive phase. The portion illustrated to the right of C includes a second "drive" portion akin to the portion from A to B. Those of ordinary skill will appreciate that, as explained above, the overall shape of the curve illustrated in FIG. 1, its smoothness, the slope of the rising and falling line from A to B, and the relative distance from A to B and B to C all provide qualitative data concerning a particular oarsman's style, or that of an entire crew if the data from each member are overlaid.

The details of a preferred embodiment of the apparatus of the present invention are illustrated in FIG. 2. As shown, the force sensing stretcher assembly is preferably affixed to the keel 1 of the shell or other rowing apparatus and the attached slotted keel track 2. As explained above, the resultant force F is applied at some instant by the oarsman's feet to the footboard 3 during the driving phase. The vector F will be directed into the footboard during the drive phase and away from the footboard during the recovery phase. The broken arrow labeled X is drawn to denote the positive-x-direction.

Figure 3:
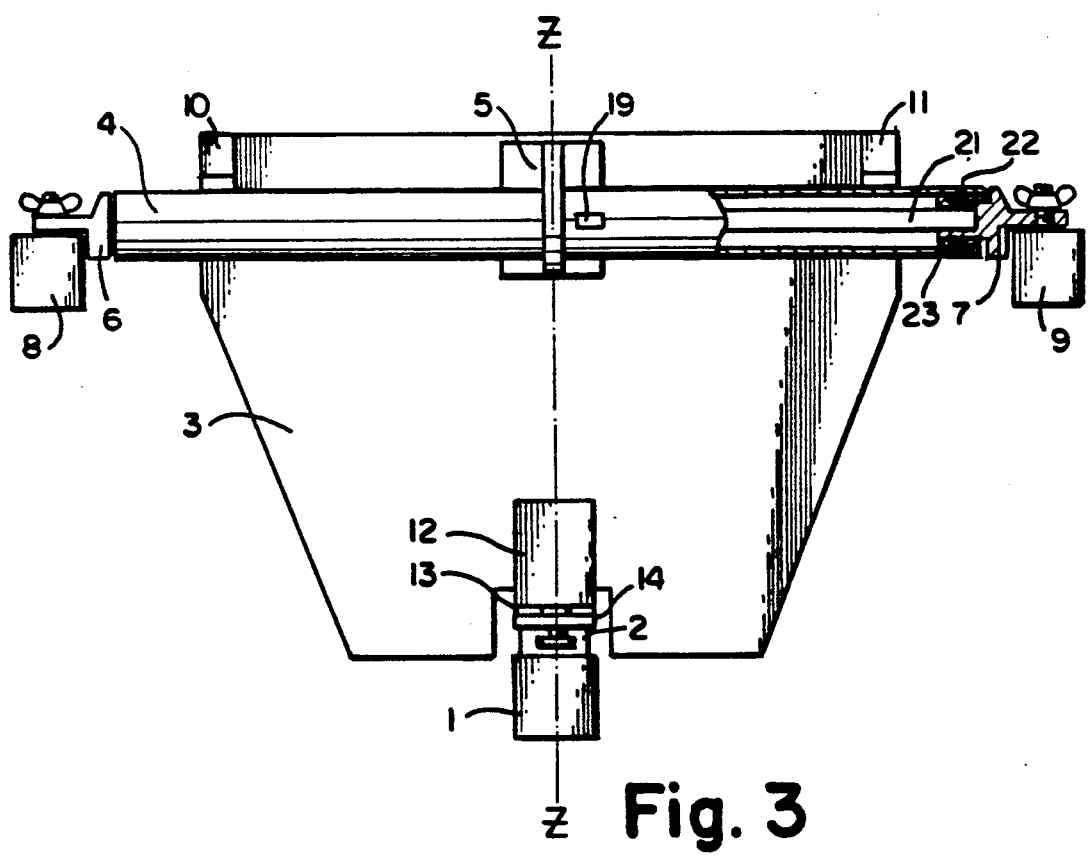
FIG. 3 is a front elevation view, partially sectioned, of the apparatus depicted in FIG. 2.

Referring now to FIG. 3, a front view of the apparatus illustrated in FIG. 2 is shown, looking toward the bow of the rowing apparatus. The upper part of the footboard 3 is hingably attached to the midpoint of a flexural member, which is preferably a transverse support tube 4 such as that illustrated. The footboard is preferably attached near the center of the transverse member by a right angle bracket 5. The end fittings, or end plugs, 6,7 are fastened respectively to the port and starboard rails, 8,9, which are an integral part of the hull structure or other mounting point on the rowing apparatus. Guide blocks 10,11 prevent the rotation of the footboard 3 about the axis Z—Z illustrated in FIG. 3, but do not restrict movement in the X-direction shown in FIG. 2.

Figure 4A:
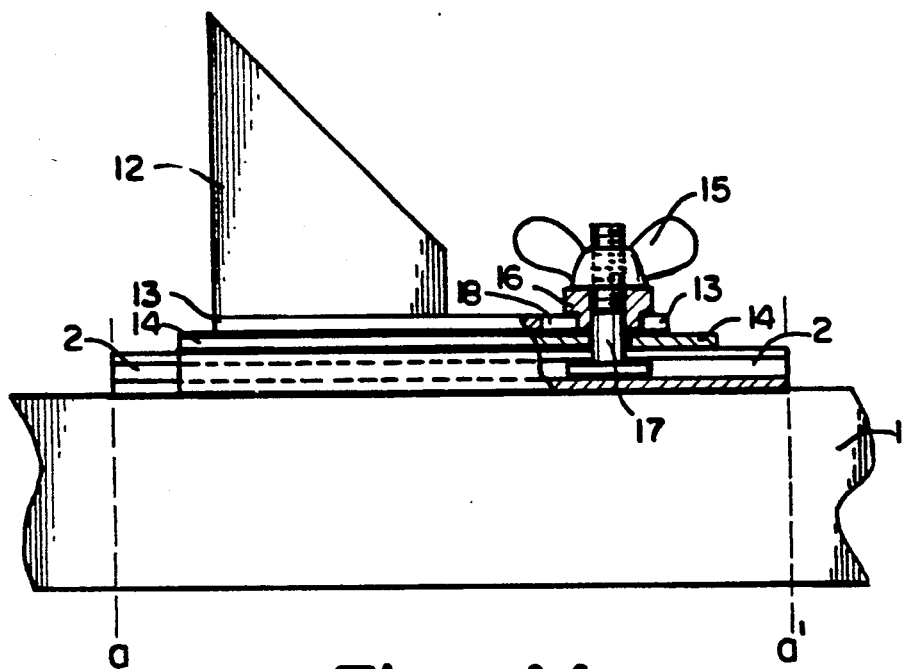
FIG. 4A is a partially broken away side elevation view of a portion of the apparatus depicted in FIG. 2.
Figure 4B:
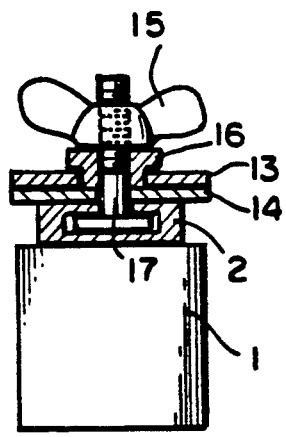
FIG. 4B is a rear elevation view of the portion of the apparatus of the present invention illustrated in FIG. 4A.
Figure 4C:
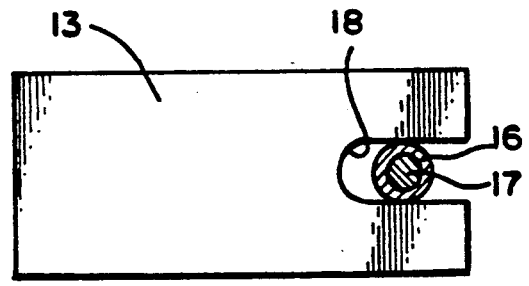
FIG. 4C is a top plan view, taken through section C—C, of the portion of the apparatus of the present invention illustrated in FIG. 4A-4B.

The lower end of the footboard 3 is attached to a vertical support 12, to which a sliding shoe 13 is affixed. The sliding shoe 13 rests on a base plate 14 which can be clamped to the slotted track 2. Referring to FIG. 4A, it can be seen that the baseplate 14 and the slotted track 2 are clamped by compression between the flanged guide bushing 16 and the head of a T-bolt 17, but the T-bolt remains free to move. As illustrated in FIG. 4B, when the wing nut 15 is tightened, sufficient clearance remains between the flange of the bushing 16 and the shoe 13 to allow it to move freely. FIG. 4C illustrates how this movement is constrained to the X-direction by the slot 18 which engages the body of the guide bushing 17.

There are many possible mechanical arrangements for achieving one dimensional motion, such as that provided by the apparatus discussed above, e.g., linkages and the like, however, the sliding shoe configuration of the present invention has two practical advantages, namely, the point of sliding contact is as close to the keel 1 of the shell and as far from the transverse support tube 4 as possible. As a consequence, the lateral forces which might be developed due to the uneven application of force by the oarsman's feet are minimized. This effect is not present with standard stretchers because the footboard is rigidly attached to the transverse support tube 4.

Those of ordinary skill will realize that if the coefficient of friction between the sliding shoe 13 and base plate 14, and also between the guide blocks 10,11 and the transverse support tube 4, can be minimized, the associated frictional forces can be neglected compared to the effective force, $F_x$, transmitted to the center of the transverse support tube 4, or other flexural member, by the right angle bracket 5. As a consequence, the transverse support tube 4 will bend slightly, causing the wall of the tube to be elongated on one side and compressed on the other. As well known to those of ordinary skill, the change in length per unit length is known as strain. If the deflection of a flexural member such as the transverse support tube 4 is within the elastic range of the tube material, the strain will be directly proportional to the applied force. In the application of the present invention, it is the strain induced in the horizontal plane which is of primary interest. Strain can be measured conveniently by standard methods based on the change in electrical resistance of a sensing element such as a strain gauge which is bonded to the flexing member. The theory and practice of strain gauge measurements is well established and understood by those of ordinary skill.

Referring again to FIG. 2, in a preferred embodiment of the present invention a pair of identical strain gauges 19,20 are bonded near the middle of the transverse support tube 4 at positions diametrically opposed to each other and centered on the horizontal plane which passes through the axis of the transverse support tube 4. Not only does this increase the sensitivity of the system by a factor of two, but also makes it possible to cancel out the effects of thermal expansion of the materials used to make components such as the transverse tube support 4.

For precise calibration and reliability, the transverse support tube 4 is preferably supported in such a way that the active length is well defined and no restoring moments (torques) are generated at its ends. The existence of such moments could be particularly troublesome if the end plugs 6,7 shown in FIG. 3 were an integral part of the transverse support tube 4. In such an embodiment an unknown and perhaps variable torque load could develop at the points of attachment between the transverse support tube 4 and the rowing apparatus. Also, the flexing of the transverse tube 4 could cause excessive wear at these points of attachment. To prevent this from happening, a rigid alignment rod 21 is preferably inserted into each end plug 6,7 as shown in the cross-sectioned portion of FIG. 3. The cylindrical body of each plug 6,7 is provided with an undercut 22 as shown leaving a peripheral ridge or flange 23 upon which the transverse tube 4 is located, and which allows the active portion to deflect without generating an opposing torque. The provision of the flange 23 also uniquely and precisely defines the length involved in the strain measurements referred to above. This predetermined active length permits highly accurate and repeatable strain measurements.

The present invention utilizes a sensing system that, regardless of the type of sensor used, produces a signal, generally in the form of a voltage, that is directly proportional to the longitudinal component of force, $F_x$, acting on the foot stretcher 3 as a continuous function of time. The signal is processed by standard methods well known to those of ordinary skill and may be displayed graphically, illustrated in FIG. 1, or alternatively as an analog or digital signal from each individual oarsman and/or collectively to the coxswain or coach as desired. The real time output of the effective force or impulse can be presented as instantaneous value, i.e., directly as a function of time, or as averages taken sequentially over one or more strokes. In addition to the real time presentation, the data can be stored, for example on magnetic tape or in a solid state memory device for subsequent review and analysis. The analysis can be extended to the calculation of work and power if displacements and speed are known.

The design of the preferred embodiment of the present invention illustrated in FIGS. 2-4 provides a simple and rugged apparatus which may be readily adapted and placed in existing shells. The apparatus of the present invention neither adds significantly to the weight of the shell nor impedes its normal operation. The strain gauges are located in a relatively unobtrusive position and may be appropriately ruggedized and waterproofed, as is well known in the art. The apparatus of the present invention is largely self-contained and may be easily removed and transferred to another suitably adapted shell or other rowing apparatus.

In addition to the apparatus disclosed, the present invention also provides methods for determining the effective force applied by an oarsman. By providing a footboard assembly and flexural member as shown and discussed above and determining the strain produced by a force applied to the footboard, the effective force can be determined by converting data relating to the strain in the flexural member to force data. Most preferably, this is achieved in an automated fashion using the voltage signals produced by the strain gauges and processing techniques and apparatus well known in the art to create a force-time curve such as that illustrated in FIG. 1.

Although certain embodiments of the present invention have been described with particularity, the present invention is not meant to be limited thereby. Numerous enhancements and modifications will immediately present themselves to those of ordinary skill upon reviewing the foregoing disclosure. Accordingly, reference should be made to the appended claims to determine the full scope of the present invention.

What is claimed is:

1. Apparatus for determining the effective force generated by an athlete acting upon a rowing apparatus comprising:
    a flexural member attached to the rowing apparatus;
    a footboard having an upper end and a lower end, the footboard being hingably attached to the flexural member at its upper end and slidably attached to the rowing apparatus at its lower end; and
    strain gauge means for producing a signal indicative of the strain in the flexural member.

2. The apparatus of claim 1, wherein the rowing apparatus is a shell.

3. The apparatus of claim 1, wherein the rowing apparatus is a rowing simulator.

4. The apparatus of claim 1, wherein the flexural member is deflected by the application of a force over a predetermined length.

5. The apparatus of claim 4, wherein the flexural member is a tubular structure having two ends, each end fitted with end plug means for attaching the flexural member to the rowing apparatus and defining the predetermined length over which the flexural member may deflect.

6. The apparatus of claim 4, wherein the torque created between the flexural member and the rowing apparatus by the application of force to the flexural member is substantially eliminated.

7. The apparatus of claim 1, wherein the strain gauge means for producing a signal indicative of the strain in the flexural member are affixed to determine the strain in a horizontal plane.

8. The apparatus of claim 1, wherein the footboard is slidably attached to the rowing apparatus by the sliding engagement of a T-shaped member and a slot.

9. The apparatus of claim 8, wherein at least a portion of the T-shaped member is threaded and is retained within the slot by a nut threaded on to the T-shaped member and further comprising a bushing, whereby the T-shaped member remains free to slide in the longitudinal direction.

10. The apparatus of claim 1, further comprising processor means for converting the signal indicative of the strain in the flexural member to a signal indicative of the effective force.

11. The apparatus of claim 10, further comprising storage means for storing data comprising a representation of the signal indicative of the effective force.

12. The apparatus of claim 10, further comprising transmitter means for transmitting data comprising a representation of the signal indicative of the effective force.

13. Apparatus for determining the effective force generated by an athlete acting upon a rowing apparatus comprising:
    a tubular flexural member having two ends, each attached to the rowing apparatus by an end plug;
    a footboard having an upper end and a lower end, the footboard being hingably attached to the flexural member at its upper end and slidably attached to the rowing apparatus at its lower end;
    strain gauge means for producing a signal indicative of the strain in a horizontal plane of the flexural member; and
    processor means for converting the signal indicative of the strain in the flexural member to a signal indicative of the effective force,
    whereby the end plugs attached to each end of the tubular flexural member substantially eliminate the torque created by the force applied to the footboard and define a predetermined length over which the flexural member deflects.

14. The apparatus of claim 13, wherein the rowing apparatus is a shell.

15. The apparatus of claim 13, wherein the rowing apparatus is a rowing simulator.

16. The apparatus of claim 13, further comprising storage means for storing data comprising a representation of the signal indicative of the effective force.

17. The apparatus of claim 13, further comprising transmitter means for transmitting data comprising a representation of the signal indicative of the effective force.

18. A method of determining the effective force generated by an athlete acting upon a rowing apparatus comprising the steps of:
    providing a footboard having an upper end and a lower end, the footboard being hingably attached at its upper end to a flexural member attached to the rowing apparatus and slidably attached at its lower end to the rowing apparatus;
    determining the strain in the flexural member;
    producing a signal indicative of the strain in the flexural member; and
    converting the signal indicative of the strain in the flexural member to a signal indicative of the effective force.

19. The method of claim 18, further comprising the step of transmitting data comprising a representation of the signal indicative of the effective force.

20. The method of claim 18, further comprising the step of storing data comprising a representation of the signal indicative of the effective force.

* * * * *